(12) United States Patent
Shekalim

(10) Patent No.: US 10,376,413 B2
(45) Date of Patent: Aug. 13, 2019

(54) IMPLANTABLE DRUG DELIVERY DEVICE AND A SYSTEM AND METHOD FOR DEPLOYMENT OF SUCH DEVICES

(71) Applicant: MICROSERT LTD., Omer (IL)

(72) Inventor: Avraham Shekalim, Nesher (IL)

(73) Assignee: MICROSERT LTD., Omer (IL)

( * ) Notice: Subject to any disclaimer, the term of this patent is extended or adjusted under 35 U.S.C. 154(b) by 204 days.

(21) Appl. No.: 15/030,381

(22) PCT Filed: Oct. 27, 2014

(86) PCT No.: PCT/IB2014/065634
§ 371 (c)(1),
(2) Date: Apr. 19, 2016

(87) PCT Pub. No.: WO2015/059680
PCT Pub. Date: Apr. 30, 2015

(65) Prior Publication Data
US 2016/0270955 A1   Sep. 22, 2016

Related U.S. Application Data

(60) Provisional application No. 61/896,079, filed on Oct. 27, 2013.

(51) Int. Cl.
*A61M 5/148* (2006.01)
*A61F 9/00* (2006.01)
*A61M 5/152* (2006.01)
*A61M 5/142* (2006.01)
*A61M 25/10* (2013.01)

(52) U.S. Cl.
CPC ....... *A61F 9/0017* (2013.01); *A61M 5/14276* (2013.01); *A61M 5/152* (2013.01); *A61M 25/10* (2013.01); *A61M 2025/1047* (2013.01); *A61M 2025/1054* (2013.01); *A61M 2210/0612* (2013.01)

(58) Field of Classification Search
CPC .. A61F 9/0017; A61F 9/00; A61F 2/00; A61F 5/0013; A61M 25/10; A61M 2025/1004; A61M 2205/04; A61M 5/145; A61M 5/148; A61M 5/1483; A61M 2005/14513; A61M 31/002; A61K 9/00
USPC .......................................... 604/99.01, 102.02
See application file for complete search history.

(56) References Cited

U.S. PATENT DOCUMENTS

| 4,351,341 A | * | 9/1982 | Goldberg | A61B 17/22032 600/587 |
| 4,444,188 A | * | 4/1984 | Bazell | A61B 17/22032 604/103 |
| 5,573,509 A | * | 11/1996 | Thornton | A61M 25/104 604/102.02 |

(Continued)

*Primary Examiner* — Bhisma Mehta
*Assistant Examiner* — Hong-Van N Trinh
(74) *Attorney, Agent, or Firm* — Mark M. Friedman

(57) ABSTRACT

A drug delivery device is formed from an elastic sleeve deployed around a core, with first and second edge portions inwardly inverted. When a fluid is introduced between the core and the sleeve, the sleeve inflates to form a reservoir with a pressure of the fluid pressing the inwardly-inverted extremities portions against the core. The device is preferably anchored by providing a stem of conformable material which is depressed by pressure applied by adjacent edges of a layer of tissue to achieve tissue-wedged anchoring of the device.

17 Claims, 10 Drawing Sheets

(56) References Cited

U.S. PATENT DOCUMENTS

| | | | | |
|---|---|---|---|---|
| 6,261,260 | B1 * | 7/2001 | Maki | A61L 29/04 428/35.5 |
| 8,486,052 | B2 * | 7/2013 | Varner | A61F 9/0017 424/424 |
| 2006/0025726 | A1 * | 2/2006 | Fischer, Jr. | A61M 25/0017 604/265 |
| 2009/0198216 | A1 * | 8/2009 | Muni | A61B 17/24 604/514 |
| 2012/0184905 | A1 * | 7/2012 | Shekalim | A61M 5/14248 604/132 |
| 2012/0277811 | A1 * | 11/2012 | Lauchner | A61B 17/8855 606/86 R |

* cited by examiner

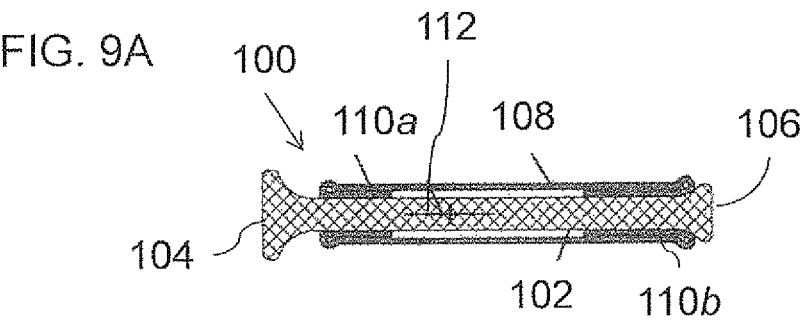
FIG. 9A
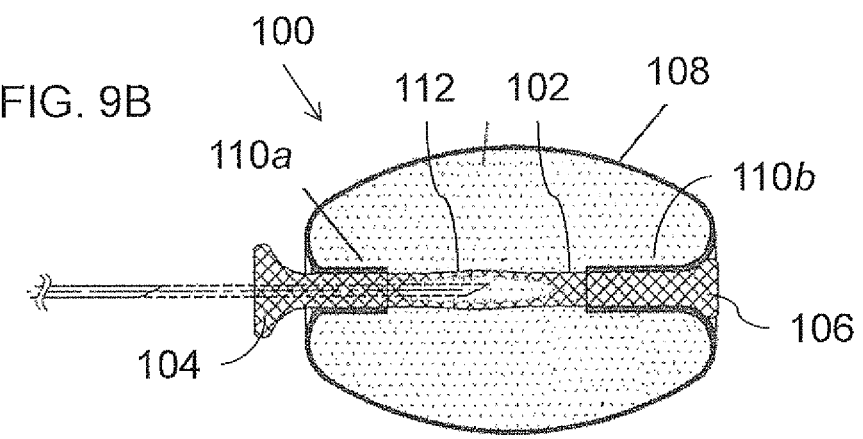
FIG. 9B
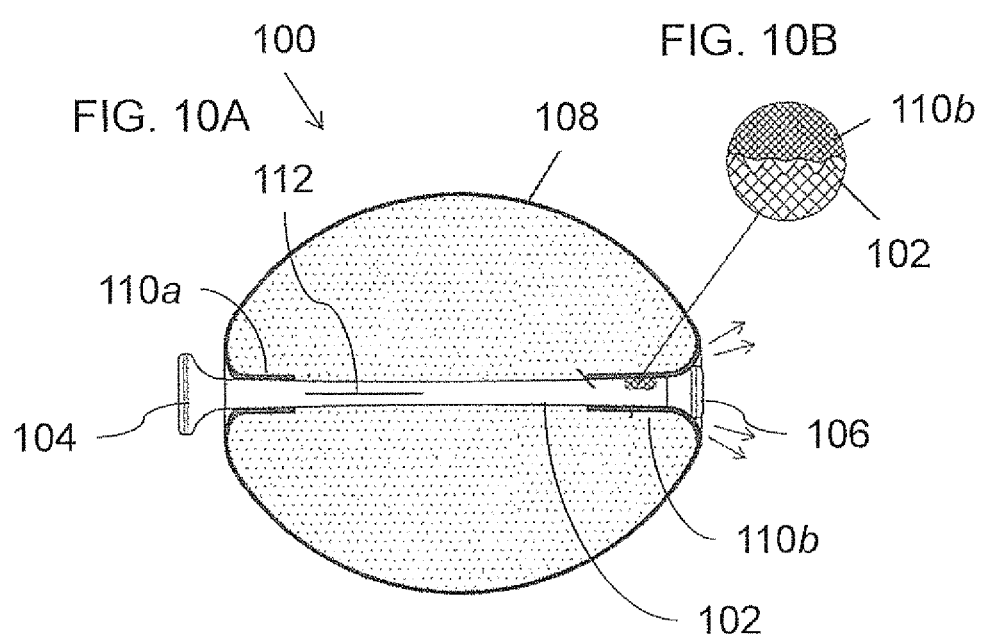
FIG. 10A
FIG. 10B

FIG. 13A
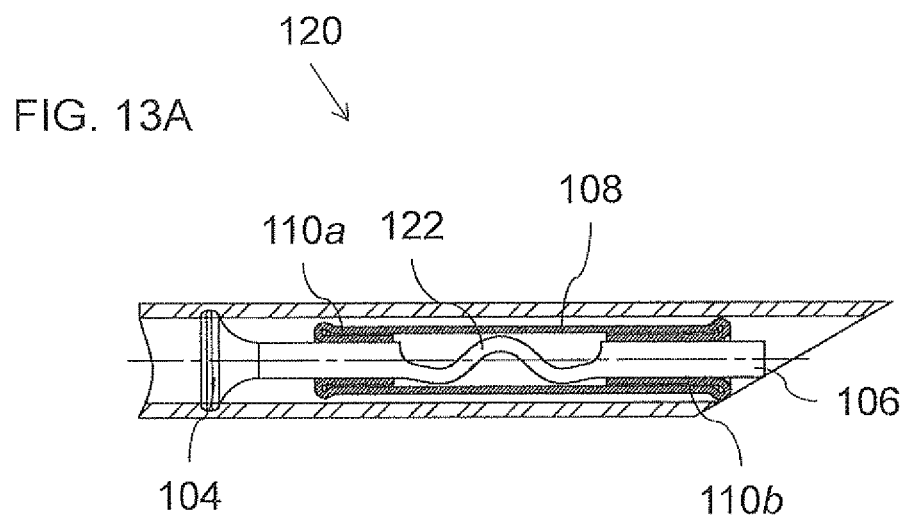
FIG. 13B
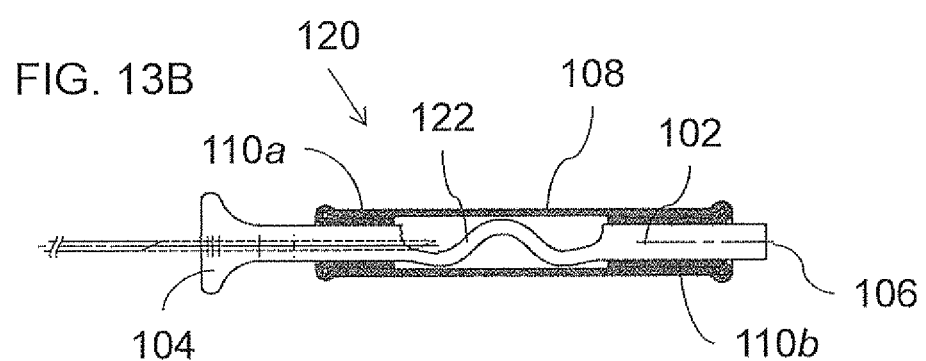
FIG. 13C
FIG. 13D
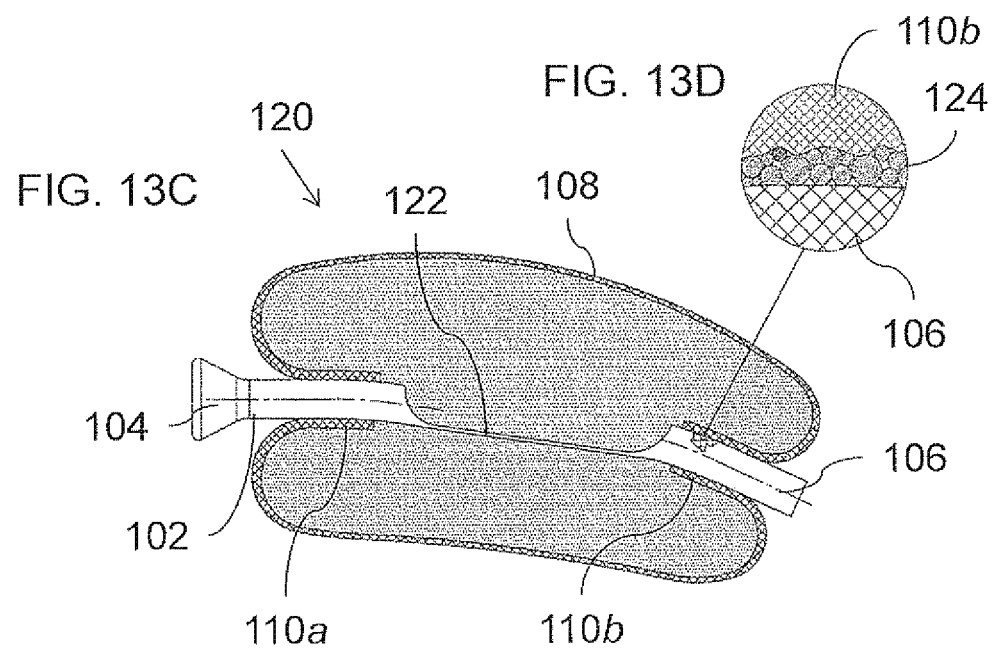

IMPLANTABLE DRUG DELIVERY DEVICE AND A SYSTEM AND METHOD FOR DEPLOYMENT OF SUCH DEVICES

FIELD AND BACKGROUND OF THE INVENTION

The present. Invention relates to implantable drug delivery devices and, in particular, it concerns drug delivery devices suitable, for example, for deployment anchored in a layered biological structure, with particular applicability to ocular drag delivery. The invention also provides systems and methods for deployment and anchoring of implantable drug delivery devices.

Background to the present invention may be found in she following patent publications:

WO 2012/131583, which describes a delivery system and corresponding method for deploying and filling drug delivery devices from a canula.

US 2012/0184905, which discloses various implantable inflatable drug reservoirs in which fluid release occurs via small passageways defined within a central core or in a region of overlap between a layer of the reservoir wall and the central core.

U.S. Pat. No. 5,466,233, US 2003/0014036, WO 2010/0088548 and U.S. Pat. No. 8,399,006 alt disclose various slow-release drug delivery devices for ocular applications.

SUMMARY OF THE INVENTION

The present invention is an implantable drug delivery device, and a system and method for deployment of such devices.

According to the teachings of an embodiment of the present invention there is provided, (a) a core; and (b) a sleeve deployed around the core, the sleeve having first and second portions inwardly inverted and having elastic properties such that when a fluid is introduced between the core and the sleeve, the sleeve inflates to form a reservoir with a pressure of the fluid pressing the inwardly-inverted portions against the core.

According to a further feature of an embodiment of the present invention, the core extends beyond the first inwardly inverted portion of the sleeve to provide a core extension, the core extension being conformable by pressure applied by adjacent edges of a layer of tissue to facilitate tissue-wedged anchoring.

According to a further feature of an embodiment of the present invention, the core is formed from a material having a Shore-A hardness in the range from 20 to 70, and most preferably in the range from 30 to 45.

According to a further feature of an embodiment of the present invention, the core and the sleeve are formed primarily from silicone rubber.

According to a further feature of an embodiment of the present invention, the sleeve is formed with a constant cross-section formed by extrusion.

According to a further feature of an embodiment of the present invention, the core has an intermediate portion having a direction of elongation and extending for a majority of a length of the core, the intermediate portion having a first maximum lateral dimension, and wherein a first end of the core is formed with a region having two lateral dimensions greater than the first maximum lateral dimension.

According to a further feature of an embodiment of the present invention, the core has an intermediate portion having a direction of elongation, wherein the intermediate portion is formed with a slit parallel to the direction of elongation extending along at least part of a length of the intermediate portion.

According to a further feature of an embodiment of the present invention, the first and second inwardly inverted portions of the sleeve contact first and second regions of the core, respectively, and wherein the core has an intermediate portion between the first and second regions, the intermediate portion having a cross-sectional area no more than half a cross-sectional area of the first and second regions of the core.

According to a further feature of an embodiment of the present invention, the core has a direction of elongation, a majority of a length of the core being generally cylindrical, and wherein at least one end of the core is outwardly flared.

According to a further feature of an embodiment of the present invention, the core is formed from elastomeric material and wherein, during inflation of the reservoir, a length of the core increases.

According to a further feature of art embodiment of the present invention, the core and the sleeve are configured such that, when the reservoir is inflated, the core deploys asymmetrically within the reservoir.

According to a further feature of an embodiment of the present invention, the reservoir contains a liquid medication, and wherein properties of the sleeve and of the liquid medication are such that diffusion of the liquid medication through the sleeve occurs as a therapeutically relevant rate.

According to a further feature of an embodiment of the present invention, at least one of the sleeve and the core is formed with a textured surface such that a region of overlap between the at least one of the first and second extremities with the core defines at least one fluid release passageway.

According to a further feature of an embodiment of the present invention, a particulate or fibrous material is interposed between a surface of the sleeve and a surface of the core at least at a region of overlap between at least one of the first and second portions with the core, thereby defining fluid release passageways.

BRIEF DESCRIPTION OF THE DRAWINGS

The invention is herein described, by way of example only, with reference to the accompanying drawings, wherein:

FIGS. 9A and 9B are cross-sectional views of the drug delivery device of FIG. 7 when empty and during filling, respectively;

FIG. 10A is a cross-sectional view of the DDD of FIG. 9 fully inflated;

FIG. 10B is an enlarged view of a region of FIG. 10A illustrating a possible mechanism of drug release;

FIG. 13A is an enlarged schematic cross-sectional view showing a variant implementation of a drug delivery device, constructed and operative according to an embodiment of the present invention, within a canula ready for delivery;

FIG. 13B is a cross-sectional view of the drug delivery device of FIG. 13A about to be filled;

FIG. 13C illustrates the drug delivery device of FIG. 13A after filling in its state for deployment; and FIG. 13D is an enlarged view of a region of FIG. 13C illustrating a further possible mechanism of drug release.

DESCRIPTION OF THE PREFERRED EMBODIMENTS

Figure 1:
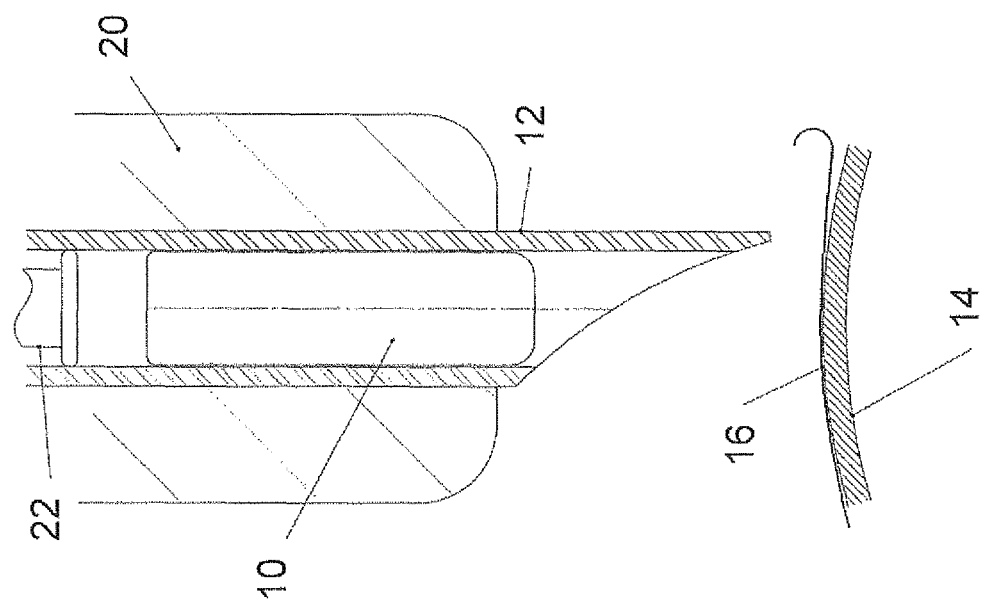
FIGS. 1-5 illustrate schematically a preferred sequence of insertion and anchoring of a drug delivery device (DDD) (as a non-limiting example of an implant) according to a method, and corresponding deployment system, of the present invention, being, shown prior to incision, during incision, after advancing of the implant, during withdrawal of the delivery system, and on completion of the procedure, respectively.

The present invention is an implantable drug delivery device, and a system and method for deployment of such devices.

The principles and operation of drug delivery devices according to the present invention may be better understood with reference to the drawings and the accompanying description.

The present invention includes a number of different aspects, each of which is believed to be patentable in its own right, and which are most preferably used together in synergy to provide a particularly advantageous drug delivery system and method. Specifically, a first aspect of the invention, described with reference to FIGS. 1-6, relates to an anchoring technique and corresponding drug delivery device structure which achieves effective anchoring of a drug delivery device to a layer of tissue, especially applicable to the ocular sclera, while minimizing trauma to the tissue. A second interrelated aspect of the invention relates to a method and corresponding delivery system for reliably deploying the drug delivery device at a desired depth of insertion relative to the tissue layer without requiring particular precision of operation by a medical practitioner. A third aspect of the present invention relates to a particularly preferred drug delivery device implant, described with references to FIGS. 7-13D, which may be used to advantage in the context of a system and method implementing the first two aspects of the invention. Each of these aspects will now be described.

Referring first to the anchoring technique of the present invention, it should be noted that many prior devices intended for anchoring in a layer of tissue employ inner and outer abutment features for contacting the internal and external surfaces of the tissue to prevent the device from being dislodged, and typically employ materials which are significantly harder than the surrounding tissues. Examples of such devices include the "tack" of U.S. Pat. No. 5,466, 233, the "fixation mechanism" of US 2003/0014036 and the "retention structure" of U.S. Pat. No. 8,399,006. All of these geometrical forms present contact surfaces that tend to rub against the tissue or otherwise cause irritation.

In contrast, to this approach, certain implementations of the present invention provide fixation of an implant primarily by what is referred to here as "tissue-wedged anchoring" in which a "stem" of the implant is formed from soft material which is conformable by pressure applied by adjacent edges of a layer of tissue to facilitate gripping of the device between adjacent edges of the tissue layer. In order to achieve this effect optimally, the implant is preferably implemented with a relatively narrow "stem" or shaft, fa relatively narrow the material of at least a stem portion of the implant is preferably chosen to have a Shore-A hardness in the range 20-70, and most preferably in the range 30-45. A particularly preferred material for implementing the stem of the implant, and in certain preferred cases the entirety of the implant, is silicone rubber. Choice of materials with these properties for the implant stem ensures that the stem conforms to the shape of any adjacent tissue edge which presses against it, thereby forming a temporary depression in the stem and allowing the tissue to achieve a mechanical purchase on the stem, thereby anchoring the device very effectively. Additionally, the conforming properties of the material enable it to fill the shape of an opening in the tissue layer, thereby facilitating sealing of the tissue layer around the incision.

In a general case, this form of anchoring can be used to advantage with substantially any type of implant and any implantation technique. For example, in the context of manually implanted devices, the device may be inserted through an incision so that the stem projects out through the incision, and the sides of the incision can then be sewn together around the stem or otherwise closed against the stem. In a particularly preferred subset of applications, the invention is implemented with a DDD that is delivered from an insertion needle ("canula"), such as is illustrated in FIGS. 1-6.

Referring to FIG. 1, the DDD is illustrated here schematically as a cylindrical implant 10 deployed within an insertion needle 12. The DDD can be any type of DDD, employing any drug delivery mechanism including, but not limited to, liquid drug dispensing, diffusion drug release, and dissolution drug release. In certain particularly preferred implementations, the DDD is a liquid drug dispensing device with an inflatable drug reservoir which is filled after introduction of part of the device through the tissue layer, and most preferably, according to the various teachings of this invention with reference to FIGS. 7-13D below. That said, for the purpose of describing the anchoring mechanism and the deployment method and system of the present invention, the preferred implementation does not detract from the generic scope of the description which remains applicable to any and all DDD technologies. The tissue anchoring technique described here is also of advantage for applications outside the field of drug delivery, for other types of implant performing monitoring functions, mechanical functions and other types of implants.

In the implementation illustrated here, the insertion needle 12 is formed with a sharp penetrating tip (beveled tip) for forming its own opening a tissue layer, exemplified here by the layer of the ocular sclera 14, which is overlaid by the conjunctiva 16. Alternative implementations employing an unsharpened needle (e.g. a cylinder with a flat tip, not shown) inserted through a pre-cut opening or flap also fall within the scope of the present invention.

Figure 2:
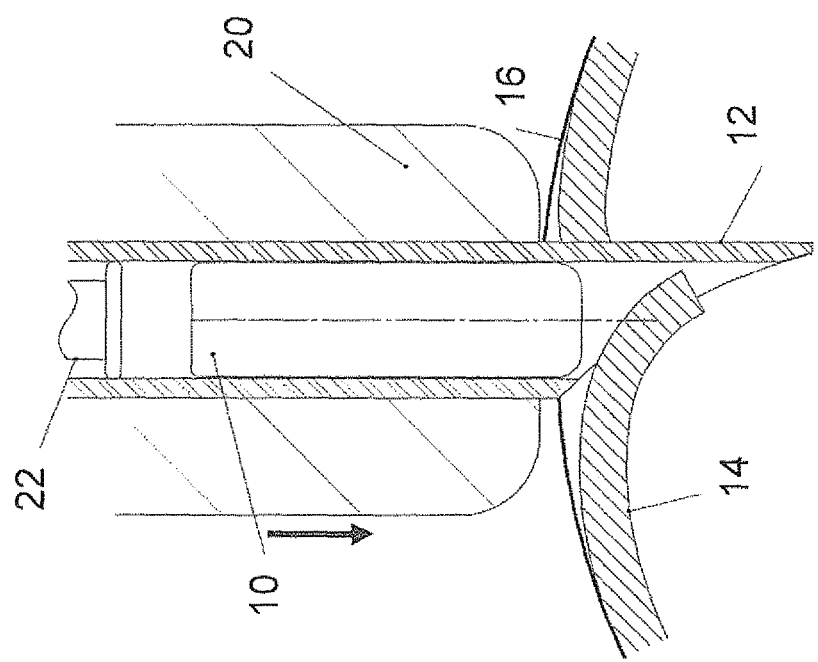
Figure 3:
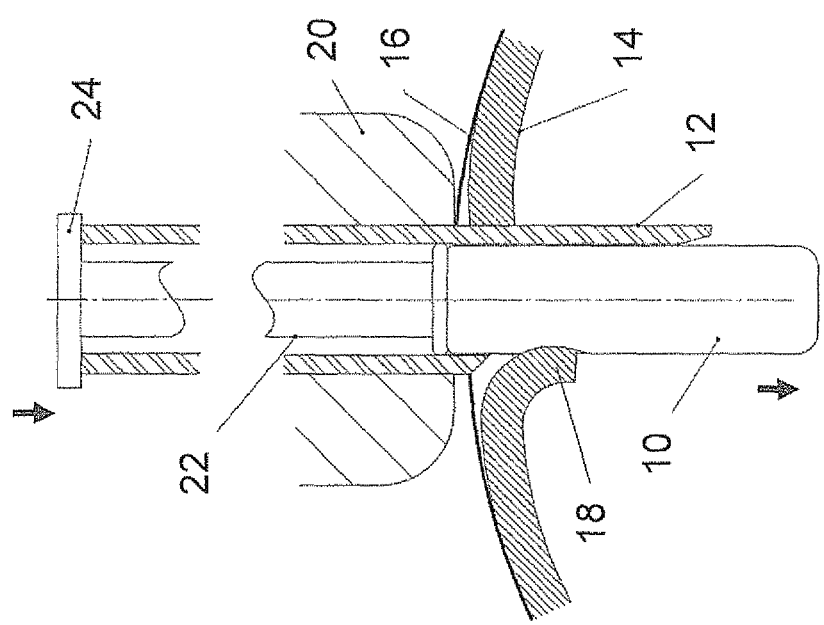
Figure 6:
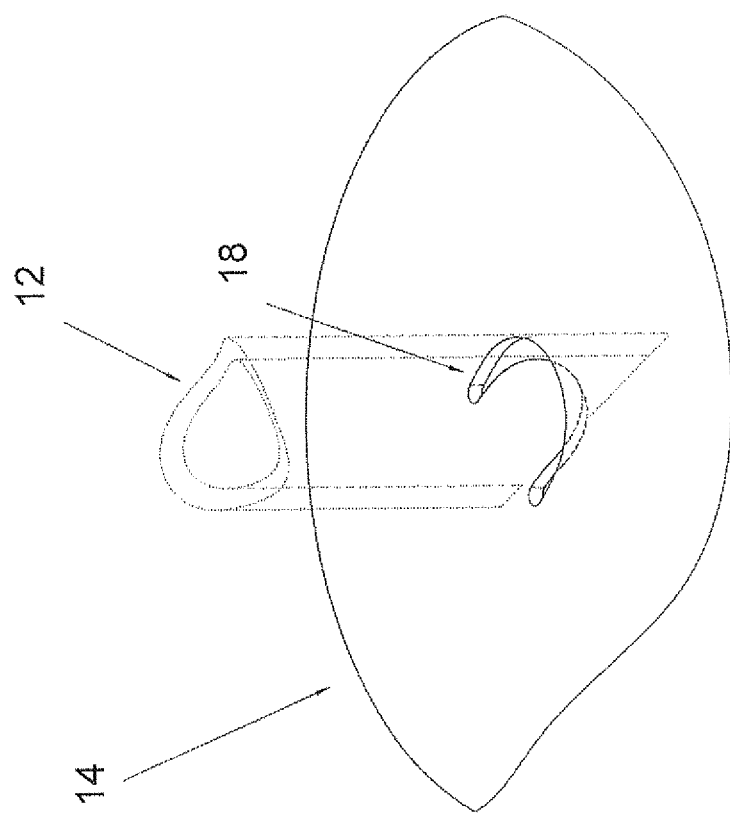
FIG. 6 is a schematic isometric view illustrating a typical shape of an opening formed by an insertion canula through a tissue layer according to an implementation of the present invention.
Figure 7:
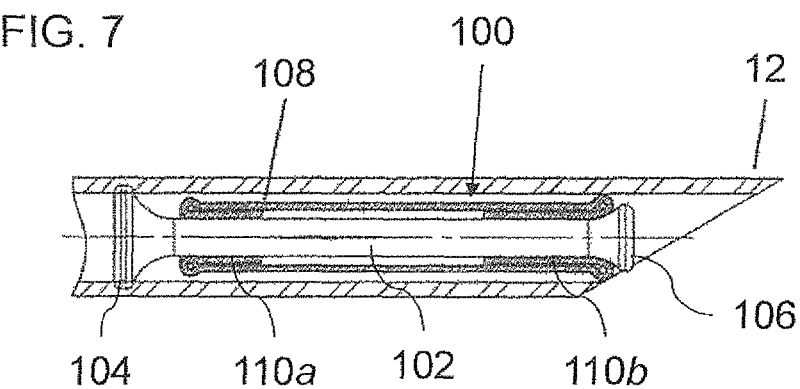
FIG. 7 is an enlarged schematic cross-sectional view showing a DDD constructed and operative according to an embodiment of the present invention within a canula ready for delivery.
Figures 8A, 8B:
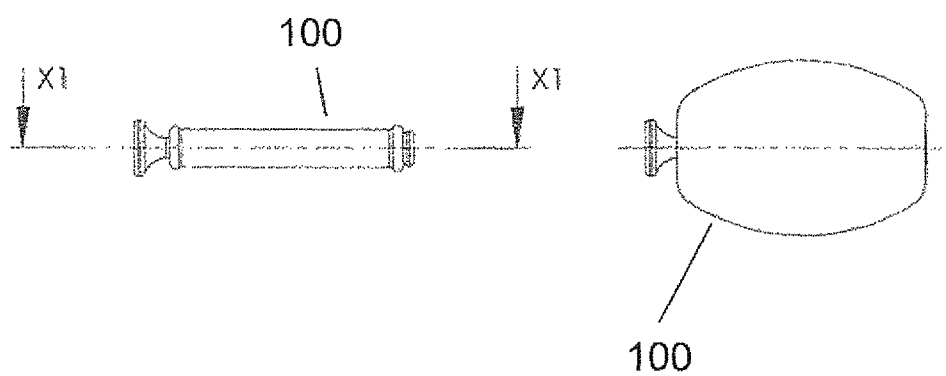
FIGS. 8A and 8B are schematic side views illustrating the drug delivery device of FIG. 7 when empty and when filled, respectively.

Penetration of insertion needle 12 is illustrated in FIG. 2. In certain preferred implementations, the depth of penetration of insertion needle 12 is limited by a non-penetrating stopper 20 deployed so as to at least partially surround insertion needle 12. It will be noted that, as best illustrated in FIG. 6, the form of incision cut by a beveled needle tip is typically an arcuate flap 18, which is then pushed aside by the advancing needle and stretched to accommodate the full diameter of the needle.

After needle 12 has penetrated, the drug delivery device 10 is advanced within the lumen of the canula, typically by advancing a plunger 22 deployed within the needle, to a partially-projecting position (FIG. 3) wherein a first part of the drug delivery device extends from the tip of the canula and a second part of the drug delivery device remains within the lumen. The partially-projecting position is preferably predefined by design of plunger 22 to limit its range of motion, represented schematically in FIG. 3 as a limiter 24. In the case of a beveled canula tip, for the purpose of this application, parts of the implant are only considered to be "within the lumen" if they are completely encircled by the periphery of the canula, whereas the part of the implant which is exposed around part of its periphery due to the bevel opening is referred to as "extending from the tip" of the canula. In order to ensure a desired stopping position of the implant relative to the tip of the canula, a plunger or other abutment element extending along the lumen is preferably limited by features of the associated advancing arrangement so that it cannot be advanced beyond the desired point, as illustrated here schematically by the "stopper" feature.

Figure 4:
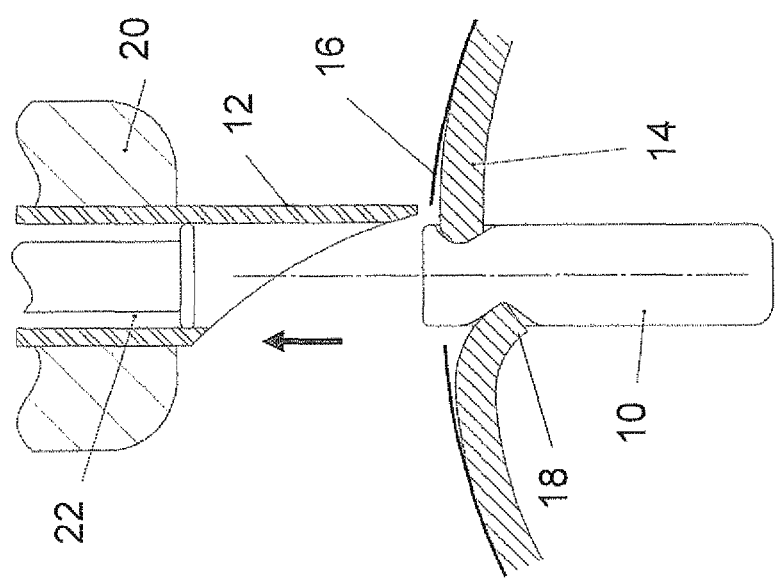
Figure 5:
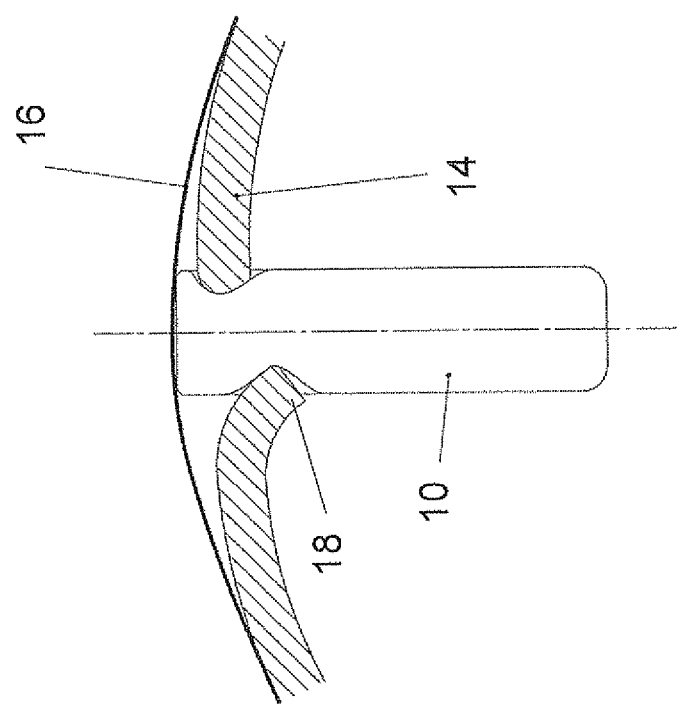

After advancing the implant as described, the canula is then gently withdrawn. The exposed first part of the implant encounters the edge of the tissue layer and, due to contact pressure of the tissue, experiences friction and/or forms a recess which engages the tissue, thereby overcoming friction between the the implant and the canula so that the implant is not withdrawn with the canula. As the canula clears the tissue, the implant is left trapped between the flap of the tissue and the surrounding tissue (in the case of ocular deployment between the flap of the sclera and the surrounding scleral tissue), as illustrated in FIGS. 4 and 5.

It should be noted that the final depth of positioning of the implant is largely independent of the depth of penetration of the deployment canula. Specifically, if the canula is inserted more deeply than shown, the outer surface of the canula will be in contact with the tissue layer, preventing contact between the tissue layer and the implant. When the canula is withdrawn to the extent that the tissue layer reaches the opening of the canula tip, only then does the tissue interact with the exposed part of the DDD, causing the remaining portion of the implant within the canula to be drawn out from the canula. As mentioned above, a tissue-stop 20 may be provided on the outside of the canula, as shown, to define a preferred depth of insertion of the delivery canula.

In the particularly preferred set of implementations employing a DDD with an inflatable reservoir for receiving a liquid drug, the liquid drug is preferably delivered via a filling needle inserted through the proximal part of the DDD so as to inflate the inflatable reservoir prior to withdrawal of the canula. Additionally, in certain preferred embodiments, the proximal end of the stem may feature an enlarged head. As described above, the anchoring mechanism of certain preferred implementations of the present invention does not rely upon any enlarged stopper feature to hold the DDD in place. However, the enlarged head may facilitate temporary gripping of the device for a refilling procedure, and provides an extra degree of safety during the refilling procedure to prevent accidental pushing of the device inwards info the body.

Referring now to further aspects of the drug delivery device aspect of the invention. FIGS. 7-11 and 13A-13D illustrate a group of implementations of a drug delivery device according to an embodiment of the present invention, with minor variations therebetween, which will be referred to genetically its the following description except where explicitly differentiated. FIG. 12, described below, illustrates an alternative embodiment of a DDD. The various embodiments of the drug delivery device described here are all preferably implemented to as to employ anchoring according to the principles described above.

Turning now to FIGS. 7-11, these show a drug delivery device, generally designated 100, which is preferably formed from only two components: a core 102 having a first (proximal) end 104 and a second (distal) end 106; and a sleeve 108 deployed around the core. The sleeve has first and second portions 110a, 110b, typically provided by opposite extremities of the sleeve, which are inwardly inverted (i.e., folded under itself). The sleeve 108 has elastic properties such that, when a fluid is introduced between the core and the sleeve, the sleeve inflates to form a reservoir with a pressure of the fluid pressing the inwardly-inverted portions against the core.

It will be appreciated that the structure described here is particulars simple for production and assembly, as further detailed below. The use of a core that spans from one side of the reservoir to the other may provide a range of advantageous properties, such as, for example, providing enhanced mechanical stability of the device in its inflated state. Optionally, the proximal end of the core is formed with a region of increased lateral dimensions, serving as a septum for injection of fluid into the reservoir. This is particularly valuable for applications in which the deployed device is to be periodically refilled, since the enlarged "mushroom" of the septum facilitates temporary gripping of the device during insertion of a refilling needle, and helps to prevent accidental forcing of the device through the tissue layer during the refilling needle insertion process. In one non-limiting case illustrated in FIGS. 7-11, both ends of the core are outwardly flared. Alternatively, as illustrated in FIGS. 13A-13C, the distal end 106 of core 102 may be formed without a flared portion. In certain alternative implementations (not shown), a uniform diameter core may be used, thereby simplifying production techniques, for example, allowing manufacture by extrusion.

Most preferably, the sleeve is a sleeve of uniform dimensions, and may be produced at low cost by extrusion techniques followed by cutting and inward folding of the ends. Typically, assembly is achieved by supporting the outer sleeve initially on a pair of tweezers from one end, slightly stretched, and employing another pair of tweezers to inwardly invert the other end of the sleeve. The sleeve is then held on a pair of tweezers from the second end while the first end is inwardly inverted. The central core can then be introduced manually within the folded sleeve while the sleeve is still slightly spread open by tweezers and the tweezers are then slid out. In some cases, it has been found helpful to insert the central core into a flat-ended hollow needle with the enlarged septum projecting therefrom to facilitate insertion into the sleeve.

In contrast to many prior art devices, it is particularly preferred that both the core and the sleeve are formed from soft materials which tend to conform to the shape of tissue that presses against the device, and thereby avoid, or at least greatly reduce, trauma and irritation to the tissue with which the drug delivery device comes in contact. The choice of materials, particularly for the core, takes on additional significance in the context of the novel anchoring technique of the present invention, as described above, and preferred ranges of material properties and preferred examples of materials are as specified in the description above.

In certain preferred embodiments, as illustrated in FIGS. 7-11, an intermediate portion of the core is formed with a slit 112 extending parallel to a direction of elongation along at least part of a length of the intermediate portion, between the regions of overlap of of portions 110a and 110b with the core. This slit is important particularly where the lateral dimensions of the core are larger than the diameter of a filling or refilling needle, to avoid the possibility that the tip of the filling needle might end up entirely surrounded by solid material. Orientation of the slit parallel to the direction of elongation of the core ensures minimal loss of tensile strength to withstand stretching of the core when the device is inflated. The overall profile of the intermediate portion of the core is preferably generally cylindrical.

Figure 11:
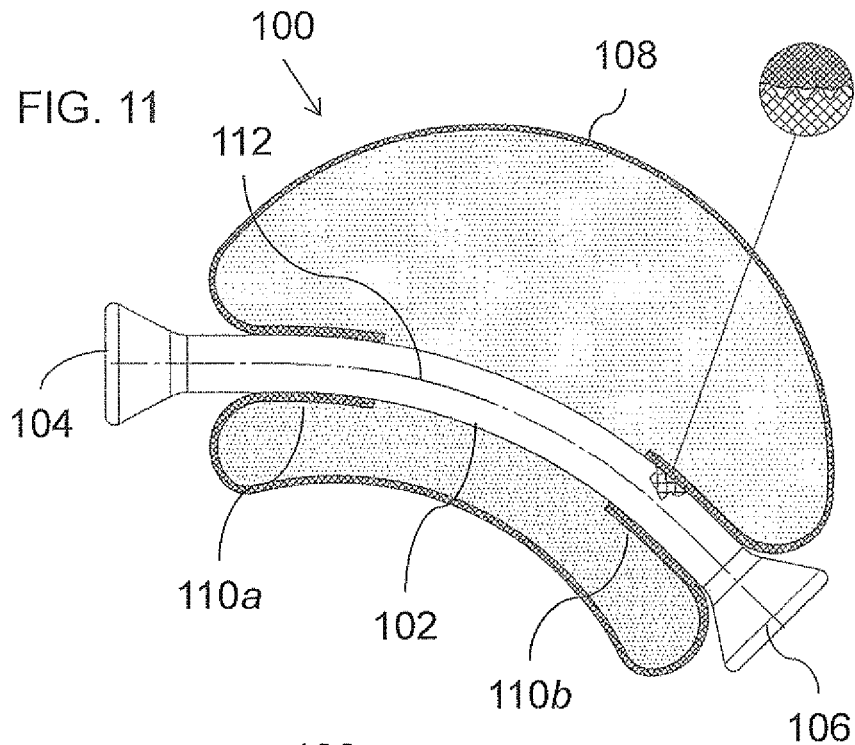
FIG. 11 is a cross-sectional view of a variant embodiment of a DDD according the present invention.

In certain particularly preferred implementations of the present invention, the core is formed from elastomeric material such that, during inflation of the reservoir, a length of the core increases. Depending on the balance of forces between tension in the inflatable membrane and tension in the core, inflation of the reservoir may result in asymmetric deployment of the core within the reservoir, forming a sort of "banana" shape, as illustrated in FIG. 11.

Turning now to FIGS. 13A-13C, this illustrates a drug delivery device, generally designated 120, which is generally similar to DDD 100, and for which equivalent features are labeled similarly. In this case, instead of slit 112, at least part of the intermediate portion of core 102 is formed with a reduced cross-sectional area, effectively forming a narrow elastic tether 122 between the proximal and distal portions of core 120. In certain preferred implementations as illustrated here in FIGS. 13A and 13B, tether 122 initially assumes a non-stretched, folded or otherwise shortened form prior to filling of the device. This together with some stretching of tether 122 as the reservoir inflates facilitates elongation of the device when assuming the inflated state of FIG. 13C. The provision of a relatively thin tether also ensures that the strain of any stretching of the core is concentrated in the tether, leaving the cross-section of the parts of the core underlying portions 110a and 110b substantially invariant. This ensures that the geometry of the seal, or the regulated flow drug release (see below), defined by these regions of contact is not affected by the degree of inflation of the reservoir.

A number of drug release mechanisms may be used by the drug delivery devices of the present invention. One particularly preferred mechanism for drug release from the DDD of the present invention is outward flow of liquid drug by permeation through the wall of the stretched reservoir, which effectively acts as a permeable membrane. By way of non-limiting example, the permeable properties of a stretched silicone rubber reservoir have been found suitable for release of a range of different liquid drugs in aqueous solution at clinically relevant rates. The exact rate of drug release may be adjusted by empirical methods, and depends on the wall thickness, pressure difference across the wall, the exact choice of material and the degree of tension in the wall. Adjustments to ensure relatively uniform rates of drug release may be achieved by designing the reservoir to provide a desired pressure profile as a function of inflated volume, as is known in the art. Additionally, or alternatively, adjustment of the drug delivery rate can be achieved by combining the porous drug release with a pressure-responsive flow regulation mechanism, preferably according to the teachings of the aforementioned US 2012/0184905, and specifically, where at least one of the sleeve and the core is formed with a textured surface such that a region of overlap between the at least one of the first and second extremities with the core defines at least one fluid release passageway. Such texturing is illustrated schematically in FIG. 10B, but may equally be implemented in the variants of FIGS. 12A-13C.

Alternatively, such a pressure-responsive flow regulation mechanism may be relied upon as the primary drug release mechanism while precautions are taken by suitable choice of materials to reduce passage of fluid through the reservoir wall.

A particular implementation of the principles described in US 2012/0184905 forms very small passageways for achieving a pressure-responsive flow regulation mechanism by applying fine powder to the core, for example, graphite powder which adheres to the core due to electrostatic forces and is then (rapped between the core and the inverted extreme of the sleeve. Alternatively, part or all of the surface of the core may be modified by application of fine polymer fibers by electro-spin coating techniques or the like. These solutions are illustrated schematically in FIG. 13D in which a particulate or fibrous material 124 is interposed between portion 110b (and/or 110a) of sleeve 108 and core 102, but may equally be implemented in the variants of FIGS. 7-12B.

Figure 12A:
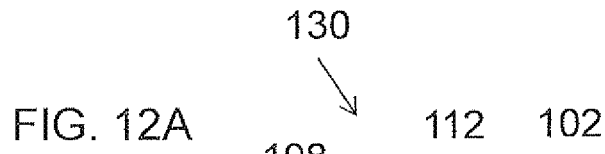
FIGS. 12A and 12B are cross-sectional view s of a further variant embodiment of a DDD according the present invention, in a production state and after assembly and filling, respectively.
Figure 12B:
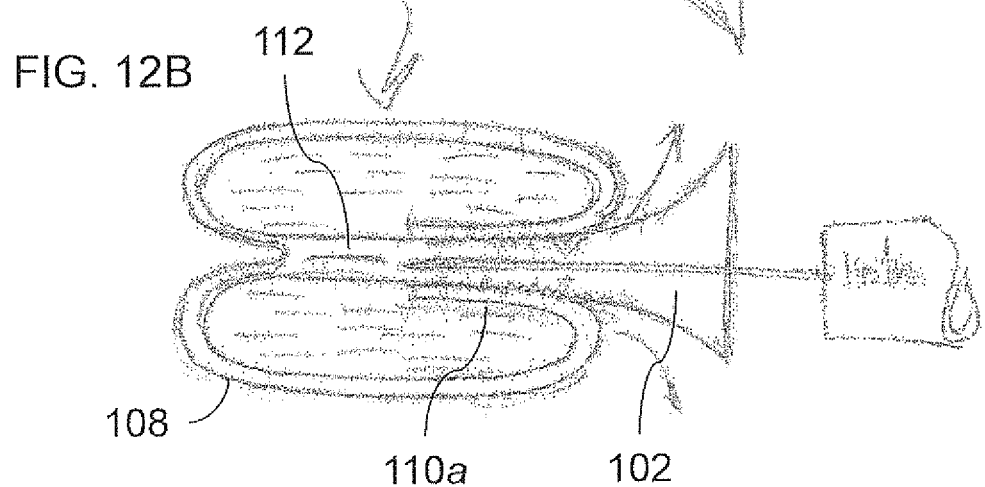

Referring briefly to FIGS. 12A and 12B, these illustrate a further variant implementation of a drug delivery device 130 which is functionally similar to the embodiments of FIGS. 7-11 and 13A-13C, but is formed from a single unitary structure which includes a core portion 102 integrated with a sleeve portion 108, manufactured in the form illustrated in FIG. 12A. The device is prepared for use by folding the end of the sleeve outwards onto itself, and then further folding the rest of the sleeve outwards around the core portion. The result is to provide an under-turned region of overlap equivalent to the seal configurations of the implementations described above. Drug release mechanisms may be by permeation through the reservoir wall and/or by pressure-responsive flow regulation at the region of overlap which, in this case, is adjacent to the filling septum and anchoring region.

To the extent that the appended claims have been drafted without multiple dependencies, this has been done only to accommodate formal requirements in jurisdictions which do not allow such multiple dependencies. It should be noted that all possible combinations of features winch would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

What is claimed is:

1. A drug delivery device comprising:
   (a) a core formed from elastomeric material; and
   (b) a sleeve deployed around said core, said sleeve having first and second portions inwardly inverted and having elastic properties such that, when a fluid is introduced between said core and said sleeve, said sleeve inflates to form a reservoir with a pressure of said fluid pressing said inwardly-inverted portions against said core, wherein at least one fluid release passageway extends between said core and at least one of said inwardly-inverted portions for slow release of the fluid,
   and wherein a proximal end of the core is configured as a septum to allow for injection of the fluid into the reservoir.

2. The drug delivery device of claim 1, wherein said core extends beyond said first inwardly-inverted portion of said sleeve to provide a core extension, said core extension being conformable by pressure applied by adjacent edges of a layer of tissue to facilitate tissue-wedged anchoring.

3. The drug delivery device of claim 2, wherein said core is formed from a material having a Shore-A hardness in the range from 20 to 70.

4. The drug delivery device of claim 2, wherein said core is formed from a material having a Shore-A hardness in the range from 30 to 45.

5. The drug delivery device of claim 2, wherein said core and said sleeve are formed primarily from silicone rubber.

6. The drug delivery device of claim 2, wherein said sleeve is formed with a constant cross-section formed by extrusion.

7. The drug delivery device of claim 1, wherein said core has an intermediate portion having a direction of elongation and extending for a majority of a length of said core, said intermediate portion having a first maximum lateral dimension, and wherein a first end of said core is formed with a region having two lateral dimensions greater than said first maximum lateral dimension.

8. The drug delivery device of claim 1, wherein said core has an intermediate portion having a direction of elongation, wherein said intermediate portion is formed with a slit parallel to said direction of elongation extending along at least part of a length of said intermediate portion.

9. The drug delivery device of claim 1, wherein said first and second inwardly-inverted portions of said sleeve contact first and second regions of said core, respectively, and wherein said core has an intermediate portion between said first and second regions, said intermediate portion having a cross-sectional area no more than half a cross-sectional area of said first and second regions of said core.

10. The drug delivery device of claim 1, wherein said core has a direction of elongation, a majority of a length of said core being generally cylindrical, and wherein at least one end of said core is outwardly flared.

11. The drug delivery device of claim 1, wherein said core is formed from elastomeric material and wherein, during inflation of said sleeve, a length of said core increases.

12. The drug delivery device of claim 1, wherein said core and said sleeve are configured such that, when said sleeve is inflated, said core deploys asymmetrically within said reservoir.

13. The drug delivery device of claim 1, wherein said reservoir contains a liquid medication, and wherein properties of said sleeve and of said liquid medication are such that diffusion of said liquid medication through said sleeve occurs as a therapeutically relevant rate.

14. The drug delivery device of claim 1, wherein at least one of said sleeve and said core is formed with a textured surface such that a region of overlap between at least one of said first and second inwardly-inverted portions with said core defines said at least one fluid release passageway.

15. The drug delivery device of claim 1, wherein a particulate or fibrous material is interposed between a surface of said sleeve and a surface of said core at least at a region of overlap between at least one of said first and second portions with said core, thereby defining said at least one fluid release passageway.

16. The drug delivery device of claim 1, wherein said inwardly-inverted portions are held against said core by elasticity and fluid pressure.

17. A drug delivery device comprising:
(a) a core formed from elastomeric material; and
(b) a sleeve deployed around said core, said sleeve having first and second portions inwardly inverted and having elastic properties such that, when a fluid is introduced between said core and said sleeve, said sleeve inflates to form a reservoir with a pressure of said fluid pressing said inwardly-inverted portions against said core, wherein at least one fluid release passageway extends between a surface of at least one of said inwardly-inverted portions facing said core and said core for slow release of the fluid.

* * * * *